United States Patent
Karasawa

(10) Patent No.: US 12,201,478 B2
(45) Date of Patent: Jan. 21, 2025

(54) ACOUSTIC WAVE PROBE AND CONTROL METHOD OF ACOUSTIC WAVE PROBE

(71) Applicant: FUJIFILM Corporation, Tokyo (JP)

(72) Inventor: Hiroyuki Karasawa, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 404 days.

(21) Appl. No.: 17/673,236

(22) Filed: Feb. 16, 2022

(65) Prior Publication Data
US 2022/0167943 A1 Jun. 2, 2022

Related U.S. Application Data

(63) Continuation of application No. PCT/JP2020/032122, filed on Aug. 26, 2020.

(30) Foreign Application Priority Data

Sep. 17, 2019 (JP) ................. 2019-168384

(51) Int. Cl.
A61B 8/08 (2006.01)
A61B 8/00 (2006.01)
A61B 8/06 (2006.01)

(52) U.S. Cl.
CPC .............. *A61B 8/488* (2013.01); *A61B 8/06* (2013.01); *A61B 8/42* (2013.01)

(58) Field of Classification Search
CPC .............. A61B 8/4472; G01S 7/52034; G01S 15/8979; H04N 19/00
See application file for complete search history.

(56) References Cited

U.S. PATENT DOCUMENTS 6,142,946 A * 11/2000 Hwang ............. A61B 8/4472
600/459
2014/0276069 A1 9/2014 Amble et al.
(Continued)

FOREIGN PATENT DOCUMENTS

JP 2003250799 A * 9/2003
JP H08308836 A * 6/2005
(Continued)

OTHER PUBLICATIONS

Broesch. The Math of DSP, Digital Signal Processing (2009). p. 69-70 (Year: 2009).*
(Continued)

*Primary Examiner* — Angela M Hoffa
*Assistant Examiner* — Younhee Choi
(74) *Attorney, Agent, or Firm* — Studebaker & Brackett PC

(57) ABSTRACT

An acoustic wave probe (2) includes a reception circuit (13) that generates a sound ray signal from a reception signal of a transducer array (11); a Doppler processing unit (15) that performs Doppler processing on the sound ray signal to generate Doppler data; a Doppler image generation unit (16) that generates a Doppler image; a compression processing unit (17) that compresses the Doppler image; a wireless communication circuit (18) that wirelessly transmits the compressed Doppler image to the information terminal; and a processing frequency setting unit (19) that sets a processing frequency F2 of the compression processing such that the processing frequency F2 becomes a frequency higher than twice a processing frequency F1 of the Doppler processing, and at least the reception circuit (13), the Doppler processing unit (15), the Doppler image generation unit (16), and the compression processing unit (17) are disposed on the same substrate (24).

20 Claims, 8 Drawing Sheets

(56) References Cited

U.S. PATENT DOCUMENTS

2016/0259040 A1   9/2016  Oshima et al.
2018/0317883 A1   11/2018 Huhtamaki et al.

FOREIGN PATENT DOCUMENTS

| JP | 2008253378 A | * | 10/2008 |
| JP | 2012-245021 A | | 12/2012 |
| JP | 2016-159089 A | | 9/2016 |
| WO | 2018/203142 A2 | | 11/2018 |

OTHER PUBLICATIONS

International Search Report issued in PCT/JP2020/032122; mailed Oct. 27, 2020.
International Preliminary Report on Patentability and Written Opinion issued in PCT/JP2020/032122; issued Mar. 15, 2022.

* cited by examiner ial No. PCT/JP2020/032122 filed on Aug. 26, 2020, which claims priority under 35 U.S.C. § 119(a) to Japanese Patent Application No. 2019-168384 filed on Sep. 17, 2019. Each of the above applications is hereby expressly incorporated by reference, in its entirety, into the present application.

BACKGROUND OF THE INVENTION

1. Field of the Invention

The present invention relates to an acoustic wave probe wirelessly connected to an information terminal and a control method of the acoustic wave probe.

2. Description of the Related Art

In the related art, in the medical field, an acoustic wave diagnostic apparatus using an acoustic wave image such as an ultrasound image has been put to practical use. Generally, the acoustic wave diagnostic apparatus has an acoustic wave probe with a built-in transducer array, and an apparatus main body connected to the acoustic wave probe, transmits acoustic waves such as ultrasonic waves toward a subject from the acoustic wave probe, receives acoustic wave echoes from the subject by the acoustic wave probe, and electrically processes the reception signals by the apparatus main body to generate an acoustic wave image.

As the acoustic wave image generated in this manner, images in various formats such as a so-called B-mode image and a Doppler image such as a power Doppler image and a continuous wave Doppler image are known. Among the acoustic wave images in various formats, in general, since the reception signal used when the Doppler image is generated is a minute signal, for example, the reception signal is easily affected by noise from various circuits arranged in the acoustic wave probe, and in the Doppler image, the waveform caused by the noise is drawn to overlap the Doppler waveform in some cases.

In order to reduce the influence of the noise in the Doppler image, for example, an ultrasound diagnostic apparatus as disclosed in JP2016-159089A has been developed. The ultrasound diagnostic apparatus of JP2016-159089A comprises a monitor of which the screen brightness is controlled by a so-called pulse width control method, and in a case where a display range on the monitor regarding speed information of a moving object represented by the Doppler image is equal to or greater than a certain range, the influence of noise caused by the voltage pulse supplied to the monitor is reduced by lowering the frequency of the voltage pulse supplied to the monitor.

SUMMARY OF THE INVENTION

In general, an acoustic wave diagnostic apparatus in which an apparatus main body and an acoustic wave probe are connected to each other by wireless communication is known. In a case where generating and displaying an acoustic wave image are performed in such an acoustic wave diagnostic apparatus, for example, it is assumed that the acoustic wave image captured by the acoustic wave probe is wirelessly transmitted, but in order to display the acoustic wave image captured by the acoustic wave probe on the monitor of the apparatus main body in real time, it is desirable to image-compress the acoustic wave image into a format such as so-called Joint Photographic Experts Group (JPEG) to reduce the information amount.

However, in the acoustic wave probe connected to the apparatus main body by wireless communication, for example, in a case where a reception circuit that processes the reception signal from the transducer array, a Doppler processing unit that processes the sound ray signal generated by the reception circuit to generate Doppler data, an image generation unit that generates an acoustic wave image consisting of a Doppler image or a B-mode image, and a compression processing unit that compresses the acoustic wave image are disposed on the same substrate, there is a problem that the waveform caused by noise is drawn to overlap the Doppler waveform in the Doppler image generated on the basis of the Doppler data by the reception signal as an analog signal, the sound ray signal as a digital signal, or the Doppler data being affected by the noise caused by the operation of the compression processing unit.

The present invention has been made in order to solve the problem in the related art, and an object of the present invention is to provide an acoustic wave probe and a control method of the acoustic wave probe which can suppress the influence of the noise caused by the operation of the compression processing unit in the Doppler image even in a case where the reception circuit, the Doppler processing unit, and the compression processing unit are disposed on at least the same substrate.

In order to achieve the object, a first acoustic wave probe according to an aspect of the present invention is an acoustic wave probe wirelessly connected to an information terminal, and the acoustic wave probe comprises: a transducer array; a transmission circuit that causes the transducer array to transmit an acoustic wave; a reception circuit that performs digital conversion of an analog reception signal acquired by the transducer array that has received an acoustic wave echo, and performs reception focusing processing to generate a sound ray signal; a Doppler processing unit that performs Doppler processing on the basis of the sound ray signal generated by the reception circuit to generate Doppler data; a Doppler image generation unit that generates a Doppler image on the basis of the Doppler data generated by the Doppler processing unit; a compression processing unit that compresses the Doppler image generated by the Doppler image generation unit; a wireless communication circuit that wirelessly transmits the Doppler image compressed by the compression processing unit to the information terminal; and a processing frequency setting unit that sets a processing frequency F2 of the compression processing in the compression processing unit such that the processing frequency F2 becomes a frequency higher than twice a processing frequency F1 of the Doppler processing in the Doppler processing unit, in which at least the reception circuit, the Doppler processing unit, the Doppler image generation unit, and the compression processing unit are disposed on the same substrate.

A second acoustic wave probe according to an aspect of the present invention is an acoustic wave probe wirelessly connected to an information terminal, and the acoustic wave probe comprises a transducer array; a transmission circuit that causes the transducer array to transmit an acoustic wave; a reception circuit that performs digital conversion of an analog reception signal acquired by the transducer array that has received an acoustic wave echo, and performs reception focusing processing to generate a sound ray signal; a Doppler processing unit that performs Doppler processing on the basis of the sound ray signal generated by the reception circuit to generate Doppler data; a B-mode image generation unit that generates a B-mode image on the basis of the sound ray signal generated by the reception circuit; a compression processing unit that compresses the B-mode image generated by the B-mode image generation unit; a wireless communication circuit that wirelessly transmits the Doppler data generated by the Doppler processing unit and the B-mode image compressed by the compression processing unit to the information terminal; and a processing frequency setting unit that sets a processing frequency F2 of the compression processing in the compression processing unit such that the processing frequency F2 becomes a frequency higher than twice a processing frequency F1 of the Doppler processing in the Doppler processing unit, and in which at least the reception circuit, the Doppler processing unit, the B-mode image generation unit, and the compression processing unit are disposed on the same substrate.

The second acoustic wave probe further comprises a Doppler image generation unit that generates a Doppler image on the basis of the Doppler data generated by the Doppler processing unit, in which the compression processing unit compresses each of the B-mode image generated by the B-mode image generation unit and the Doppler image generated by the Doppler image generation unit, and the wireless communication circuit wirelessly transmits the B-mode image and the Doppler image that are compressed by the compression processing unit.

In this case, it is preferable that the Doppler image generation unit is disposed on the substrate.

The first and second acoustic wave probe may comprise an acoustic wave transmission and reception control unit that controls transmission of the acoustic wave by the transmission circuit and reception of the acoustic wave echo by the reception circuit.

In this case, the first and second acoustic wave probes may comprise a battery; and a power supply circuit that supplies power from the battery into the acoustic wave probe.

Alternatively, the acoustic wave transmission and reception control unit may be disposed on the substrate.

In this case, it is preferable that the power supply circuit is disposed on the substrate.

The wireless communication circuit may be disposed on the substrate.

Further, the first and second acoustic wave probes may comprise a wired connection terminal for wired connection with the information terminal.

The Doppler processing unit may generate continuous wave Doppler data or pulsed Doppler data.

A first control method of an acoustic wave probe according to an aspect of the present invention is a control method of an acoustic wave probe which is wirelessly connected to an information terminal and in which at least a reception circuit, a Doppler processing unit, a Doppler image generation unit, and a compression processing unit are disposed on the same substrate, and the control method comprises causing a transducer array to transmit an acoustic wave; causing the reception circuit to perform digital conversion of an analog reception signal acquired by the transducer array that has received an acoustic wave echo, and perform reception focusing processing to generate a sound ray signal; causing the Doppler processing unit to perform Doppler processing on the basis of the generated sound ray signal to generate Doppler data; causing the Doppler image generation unit to generate a Doppler image on the basis of the generated Doppler data; causing the compression processing unit to compress the generated Doppler image; wirelessly transmitting the compressed Doppler image to the information terminal; and setting a processing frequency F2 of the compression processing such that the processing frequency F2 becomes a frequency higher than twice a processing frequency F1 of the Doppler processing.

A second control method of an acoustic wave probe according to an aspect of the present invention is a control method of an acoustic wave probe which is wirelessly connected to an information terminal and in which at least a reception circuit, a Doppler processing unit, a B-mode image generation unit, and a compression processing unit are disposed on the same substrate, and the control method comprises causing a transducer array to transmit an acoustic wave; causing the reception circuit to perform digital conversion of an analog reception signal acquired by the transducer array that has received an acoustic wave echo, and perform reception focusing processing to generate a sound ray signal; causing the Doppler processing unit to perform Doppler processing on the basis of the generated sound ray signal to generate Doppler data; causing the B-mode image generation unit to generate a B-mode image on the basis of the generated sound ray signal; causing the compression processing unit to compress the generated B-mode image; wirelessly transmitting the generated Doppler data and the compressed B-mode image to the information terminal; and setting a processing frequency F2 of the compression processing such that the processing frequency F2 becomes a frequency higher than twice a processing frequency F1 of the Doppler processing.

According to the present invention, since the acoustic wave probe comprises a reception circuit that performs digital conversion of an analog reception signal acquired by the transducer array that has received an acoustic wave echo, and performs reception focusing processing to generate a sound ray signal; a Doppler processing unit that performs Doppler processing on the basis of the sound ray signal generated by the reception circuit to generate Doppler data; a Doppler image generation unit that generates a Doppler image on the basis of the Doppler data generated by the Doppler processing unit; a compression processing unit that compresses the Doppler image generated by the Doppler image generation unit; a wireless communication circuit that wirelessly transmits the Doppler image compressed by the compression processing unit to the information terminal; and a processing frequency setting unit that sets a processing frequency F2 of the compression processing in the compression processing unit such that the processing frequency F2 becomes a frequency higher than twice a processing frequency F1 of the Doppler processing in the Doppler processing unit, even in a case where at least the reception circuit, the Doppler processing unit, the Doppler image generation unit, and the compression processing unit are disposed on the same substrate, the influence of noise caused by the operation of the compression processing unit in the Doppler image can be suppressed.

DESCRIPTION OF THE PREFERRED EMBODIMENTS

Hereinafter, embodiments of the invention will be described with reference to the accompanying drawings.

The description of configuration requirements described below is given on the basis of the representative embodiment of the present invention, but the present invention is not limited to such an embodiment.

In the present specification, a numerical range represented using "to" means a range including the numerical values before and after "to" as a lower limit value and an upper limit value.

In the present specification, the terms "same" and "identical" include an error range generally allowed in the technical field.

First Embodiment

Figure 1:
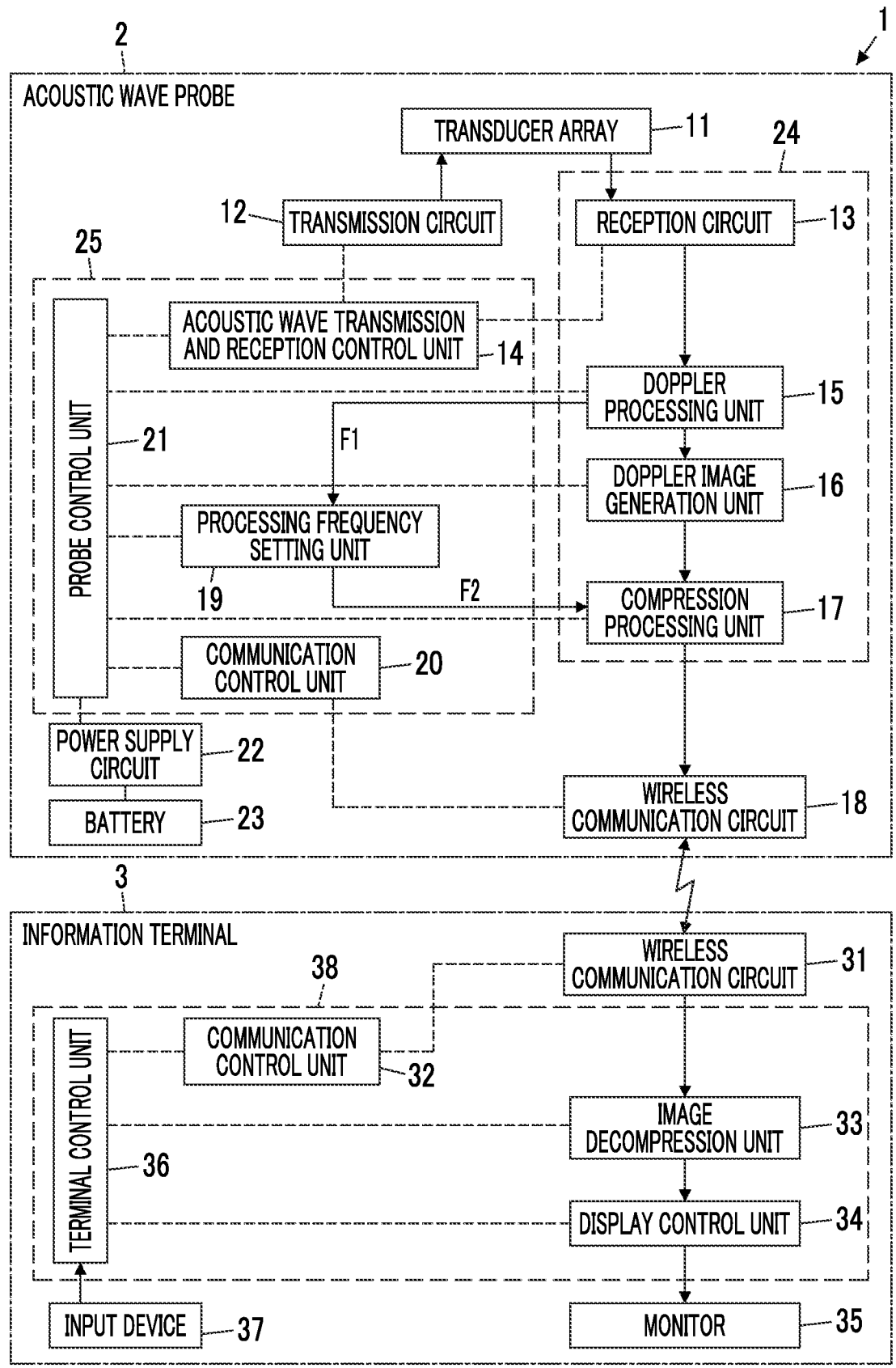
FIG. 1 is a block diagram illustrating a configuration of an acoustic wave diagnostic apparatus in a first embodiment of the present invention.

FIG. 1 illustrates a configuration of an acoustic wave diagnostic apparatus 1 in a first embodiment of the present invention. The acoustic wave diagnostic apparatus 1 is for generating an acoustic wave image such as an ultrasound image and displaying the generated acoustic wave image, and comprises an acoustic wave probe 2 and an information terminal 3. The acoustic wave probe 2 and the information terminal 3 are connected to each other by wireless communication. The acoustic wave probe 2 can be, for example, a so-called ultrasound probe, and the acoustic wave diagnostic apparatus 1 generates and displays a Doppler image such as a so-called pulse Doppler image or a continuous wave Doppler image as the acoustic wave image. The information terminal 3 can be configured by, for example, a so-called stationary personal computer, a portable thin computer called a tablet, a smartphone, and the like.

As illustrated in FIG. 1, the acoustic wave probe 2 comprises a transducer array 11, and a transmission circuit 12 and a reception circuit 13 are connected to the transducer array 11. An acoustic wave transmission and reception control unit 14 is connected to the transmission circuit 12 and the reception circuit 13. A Doppler processing unit 15, a Doppler image generation unit 16, a compression processing unit 17, and a wireless communication circuit 18 are sequentially connected to the reception circuit 13. A processing frequency setting unit 19 is connected to the Doppler processing unit 15, and the compression processing unit 17 is connected to the processing frequency setting unit 19. Further, a communication control unit 20 is connected to the wireless communication circuit 18. A probe control unit 21 is connected to the acoustic wave transmission and reception control unit 14, the Doppler processing unit 15, the Doppler image generation unit 16, the compression processing unit 17, the processing frequency setting unit 19, and the communication control unit 20. A power supply circuit 22 is connected to the probe control unit 21, and a battery 23 is connected to the power supply circuit 22.

The reception circuit 13, the Doppler processing unit 15, the Doppler image generation unit 16, and the compression processing unit 17 are disposed on the same substrate 24. The acoustic wave transmission and reception control unit 14, the processing frequency setting unit 19, the communication control unit 20, and the probe control unit 21 constitute a probe-side processor 25.

The information terminal 3 comprises a wireless communication circuit 31, and a communication control unit 32 is connected to the wireless communication circuit 31. An image decompression unit 33, a display control unit 34, and a monitor 35 are sequentially connected to the wireless communication circuit 31. A terminal control unit 36 is connected to the communication control unit 32, the image decompression unit 33, and the display control unit 34. An input device 37 is connected to the terminal control unit 36. The communication control unit 32, the image decompression unit 33, the display control unit 34, and the terminal control unit 36 constitute a terminal-side processor 38.

The transducer array 11 of the acoustic wave probe 2 illustrated in FIG. 1 has a plurality of transducers arranged in a one-dimensional or two-dimensional manner. According to a drive signal supplied from the transmission circuit 12, each of the transducers transmits an ultrasonic wave and receives an ultrasound echo from a subject to output a signal based on the ultrasound echo. For example, each transducer is configured by forming electrodes at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

The acoustic wave transmission and reception control unit 14 controls the transmission circuit 12 and the reception circuit 13 to cause the transducer array 11 to perform transmission of ultrasound beams and reception of ultrasound echoes on the basis of an inspection mode and a scanning method instructed from the probe control unit 21. Here, the inspection mode includes at least a pulsed wave Doppler mode (PW mode) and a continuous wave Doppler mode (CW mode), and also includes inspection modes such as a brightness mode (B mode) and a color flow mode (CF mode) that can be used in the acoustic wave diagnostic apparatus 1, and the scanning method indicates, for example, any one of an electronic sector scanning method, an electronic linear scanning method, an electronic convex scanning method, or the like. The acoustic wave transmission and reception control unit 14 (or probe control unit 21) sends an acoustic wave transmission and reception control reference clock to the transmission circuit 12 and the reception circuit 13.

The transmission circuit 12 includes, for example, a plurality of pulse generators, and the transmission circuit 12 adjusts the amount of delay of each drive signal so that ultrasonic waves transmitted from the plurality of transducers of the transducer array 11 form an ultrasound beam on the basis of a transmission delay pattern selected according to a control signal from the acoustic wave transmission and reception control unit 14, and supplies the obtained signals to the plurality of transducers. Thus, in a case where a pulsed or continuous-wave voltage is applied to the electrodes of the transducers of the transducer array 11, the piezoelectric body expands and contracts to generate pulsed or continuous-wave ultrasonic waves from each transducer. From the combined wave of these ultrasonic waves, an ultrasound beam is formed. For example, in the pulsed wave Doppler mode, the transmission circuit 12 generates an ultrasonic pulse from the transducer array 11 by the pulse repetition frequency PRF. The pulse repetition frequency PRF is the number of ultrasonic pulses transmitted for one second. The pulse repetition frequency PRF can be set on the basis of a user's input operation through the input device 37 of the information terminal 3, for example.

The ultrasound beam transmitted from the transducer array 11 into the subject is reflected by a target, for example, a site of the subject, and propagates toward the transducer array 11 of the acoustic wave probe 2. The ultrasound echo propagating toward the transducer array 11 in this manner is received by each transducer constituting the transducer array 11. In this case, each transducer constituting the transducer array 11 expands and contracts by receiving the propagating ultrasound echo to generate an electric signal, and outputs the electric signal to the reception circuit 13.

Figure 2:
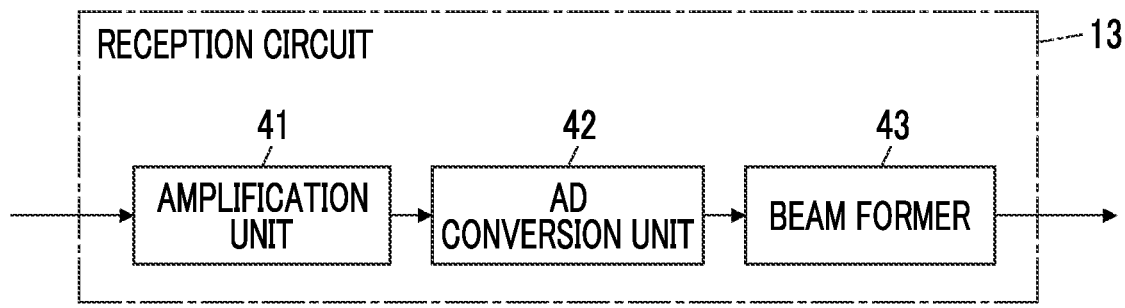
FIG. 2 is a block diagram illustrating an internal configuration of a reception circuit in the first embodiment of the present invention.

The reception circuit 13 processes the signal output from the transducer array 11 according to the control signal from the acoustic wave transmission and reception control unit 14 to generate a sound ray signal. As illustrated in FIG. 2, the reception circuit 13 has a configuration in which an amplification unit 41, an analog digital (AD) conversion unit 42, and a beam former 43 are connected in series.

The amplification unit 41 amplifies the signals input from each transducer constituting the transducer array 11, and transmits the amplified signals to the AD conversion unit 42. The AD conversion unit 42 converts the signal transmitted from the amplification unit 41 into digital reception data, and transmits the reception data to the beam former 43. The beam former 43 performs so-called reception focusing processing in which addition is performed by giving delays to respective pieces of the reception data converted by the AD conversion unit 42 according to a sound speed distribution or a sound speed set on the basis of a reception delay pattern selected according to the control signal from the acoustic wave transmission and reception control unit 14. Through the reception focusing processing, a sound ray signal in which each piece of the reception data converted by the AD conversion unit 42 is phased and added and the focus of the ultrasound echo is narrowed is acquired.

The Doppler processing unit 15 performs Doppler processing of analyzing the sound ray signal generated by the reception circuit 13 to detect a so-called Doppler shift frequency and generating Doppler data such as pulsed Doppler data or continuous wave Doppler data representing the speed of the moving object in the subject on the basis of the detected Doppler shift frequency. In this case, the processing frequency of the Doppler processing performed by the Doppler processing unit 15 is set as F1. Here, the speed of the moving object in the subject includes, for example, the speed of a blood flow in a blood vessel of the subject or the speed of a moving object such as the wall of the heart. For example, in a case where the ultrasonic pulse is transmitted into the subject by the pulse repetition frequency PRF in the pulsed wave Doppler mode, the processing frequency F1 of the Doppler processing is equal to the pulse repetition frequency PRF.

Figure 3:
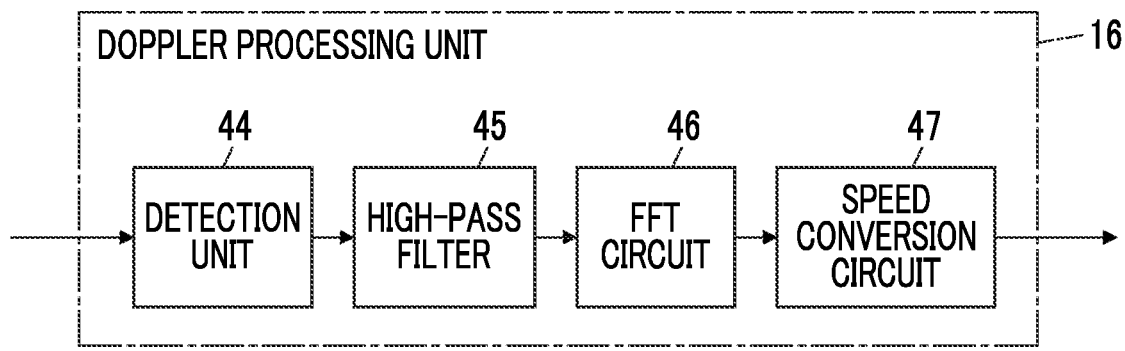
FIG. 3 is a diagram illustrating an internal configuration of a Doppler processing unit in the first embodiment of the present invention.

As illustrated in FIG. 3, the Doppler processing unit 15 has a configuration in which a detection unit 44, a high-pass filter 45, a fast Fourier transformer (FFT) circuit 46, and a speed conversion circuit 47 are connected in series.

The detection unit 44 generates a so-called complex baseband signal on the basis of the sound ray signal generated by the reception circuit 13. More specifically, the detection unit 44 mixes the sound ray signal generated by the reception circuit 13 with a carrier signal having a reference frequency to perform quadrature detection on the sound ray signal, and converts the sound ray signal into the complex baseband signal.

The high-pass filter 45 functions as a so-called wall filter, and removes a signal of a low frequency component derived from the motion of the body tissue of the subject, which is a so-called clutter signal, from the complex baseband signal generated by the detection unit 44.

The FFT circuit 46 performs Fourier transform on the complex baseband signal output by the high-pass filter 45 to generate a spectrum signal for the Doppler shift frequency.

The speed conversion circuit 47 converts information on the Doppler shift frequency in the spectrum signal generated by the FFT circuit 46 into information representing the speed of the moving object in the subject. Specifically, the speed conversion circuit 47 can calculate the information representing the speed of the moving object in the subject by a relationship of the speed V of the moving object=(C/2)×(fd/fs) by setting the Doppler shift frequency as fd, the frequency of the ultrasonic wave transmitted into the subject by the transducer array 11 as fs, the sound speed as C (about 1530 m/s), and the speed of the moving object in the subject as V. Here, the frequency fs of the ultrasonic wave transmitted into the subject can be typically about 1 MHz to 10 MHz.

Figure 4:
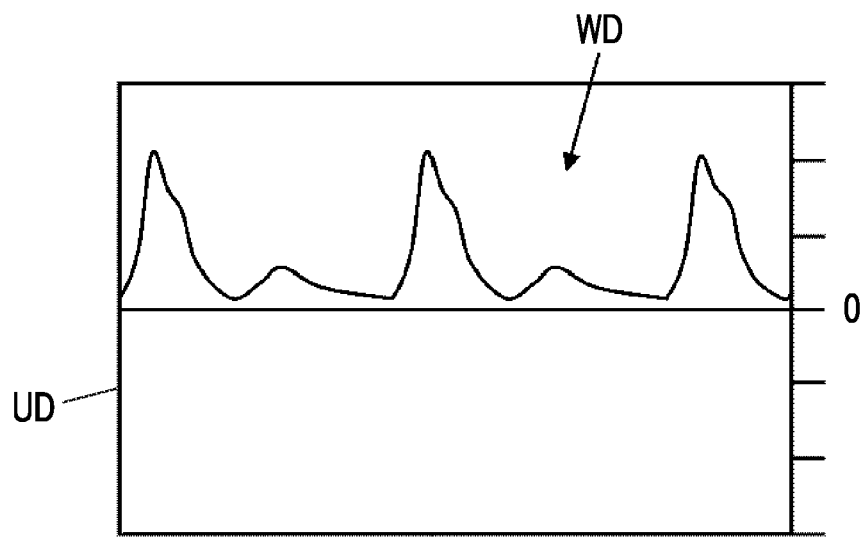
FIG. 4 is a diagram schematically illustrating an example of a Doppler image in the first embodiment of the present invention.

The Doppler image generation unit 16 generates a Doppler image such as a so-called pulse Doppler image or a continuous wave Doppler image on the basis of the Doppler data generated by the Doppler processing unit 15. More specifically, a Doppler image signal is generated by expressing the magnitude of each frequency component by brightness while aligning the Doppler data representing the speed of the moving object in the subject on a time axis. The Doppler image signal generated in such a manner is simply referred to as the Doppler image. As illustrated in FIG. 4, in a Doppler image UD, the lateral axis indicates the time axis, the vertical axis indicates the speed of the moving object in the subject, and the brightness of a Doppler waveform WD represents power in each frequency component. The display range of the Doppler waveform WD in a vertical axis direction in the Doppler image UD, that is, the speed range can be adjusted by the user's input operation through the input device 37, for example.

The compression processing unit 17 compresses the Doppler image UD generated by the Doppler image generation unit 16 according to a processing frequency F2 to reduce the information amount of the Doppler image UD. For example, the compression processing unit 17 can compress the Doppler image UD into a so-called JPEG format.

The processing frequency setting unit 19 sets the processing frequency F2 of the compression processing in the compression processing unit 17 such that the processing frequency F2 is a frequency higher than twice the processing frequency F1 of the Doppler processing in the Doppler processing unit 15.

The wireless communication circuit 18 of the acoustic wave probe 2 includes an antenna for transmitting and receiving radio waves, modulates a carrier on the basis of the Doppler image UD compressed by the compression processing unit 17, and generates a transmission signal representing the compressed Doppler image UD. The wireless communication circuit 18 transmits radio waves from the antenna by supplying the transmission signals generated in this manner to the antenna, and sequentially and wirelessly transmits the compressed Doppler image UD to the wireless communication circuit 31 of the information terminal 3. As the modulation method of the carrier, amplitude shift keying (ASK), phase shift keying (PSK), quadrature phase shift keying (QPSK), 16 quadrature amplitude modulation (16QAM), or the like is used.

The wireless communication between the wireless communication circuit 18 of the acoustic wave probe 2 and the wireless communication circuit 31 of the information terminal 3 can be performed in accordance with communication standards for mobile communication such as 5th generation mobile communication system (5G) and 4th generation mobile communication system (4G), and communication standards for short-range wireless communication such as WiFi (registered trademark), Bluetooth (registered trademark), and ultra wideband (UWB) communication system.

The communication control unit 20 of the acoustic wave probe 2 controls the wireless communication circuit 18 of the acoustic wave probe 2 such that the Doppler image UD is transmitted with a transmission radio field intensity set by the probe control unit 21. Further, the communication control unit 20 controls the wireless communication circuit 18 of the acoustic wave probe 2 such that probe control information for controlling the acoustic wave probe 2, which is wirelessly transmitted from the information terminal 3, is received.

The probe control unit 21 controls each unit of the acoustic wave probe 2 on the basis of a control program stored in advance and the user's input operation through the input device 37 of the information terminal 3.

The battery 23 is built in the acoustic wave probe 2, and supplies power to each circuit of the acoustic wave probe 2.

The power supply circuit 22 performs so-called power supply switching, and turns on or off the power supply of the acoustic wave probe 2 by connecting each circuit of the acoustic wave probe 2 and the battery 23 or disconnecting the connection thereof, under the control of the probe control unit 21.

The probe-side processor 25 having the acoustic wave transmission and reception control unit 14, the processing frequency setting unit 19, the communication control unit 20, and the probe control unit 21 is configured by a central processing unit (CPU) and a control program for causing the CPU to execute various kinds of processing, but the probe-side processor 25 may be configured by using a field programmable gate array (FPGA), a digital signal processor (DSP), an application specific integrated circuit (ASIC), a graphics processing unit (GPU), or other integrated circuits (IC) or may be configured by a combination thereof.

The acoustic wave transmission and reception control unit 14, the processing frequency setting unit 19, the communication control unit 20, and the probe control unit 21 of the probe-side processor 25 can also be configured by being integrated partially or entirely into one CPU or the like.

The wireless communication circuit 31 of the information terminal 3 includes an antenna for transmitting and receiving radio waves, receives the transmission signal wirelessly transmitted by the wireless communication circuit 18 of the acoustic wave probe 2 via the antenna, and demodulates the received transmission signal to output the Doppler image UD. Further, the wireless communication circuit 31 modulates the carrier on the basis of the probe control information input by the user through the input device 37 to generate the transmission signal representing the probe control information. The wireless communication circuit 31 wirelessly transmits the generated transmission signal to the wireless communication circuit 18 of the acoustic wave probe 2. As the modulation method of the carrier in this case, ASK, PSK, QPSK, 16QAM, or the like is used.

The communication control unit 32 of the information terminal 3 controls the wireless communication circuit 31 of the information terminal 3 such that transmission and reception of the data are performed between the wireless communication circuit 31 of the information terminal 3 and the wireless communication circuit 18 of the acoustic wave probe 2 with a transmission radio field intensity and a reception radio field intensity set by the terminal control unit 36.

The image decompression unit 33 decompresses the Doppler image UD sent from the wireless communication circuit 31 of the information terminal 3 into a format before being compressed by the compression processing unit 17.

The display control unit 34 performs predetermined processing on the Doppler image UD sent from the image decompression unit 33, and displays the processed Doppler image UD on the monitor 35.

The monitor 35 is for displaying the Doppler image UD and the like under the control of the display control unit 34, and includes a display device such as a liquid crystal display (LCD), or an organic electroluminescence (EL) display.

The input device 37 is for the user to perform an input operation, and can be configured to comprise a keyboard, a mouse, a trackball, a touchpad, a touch panel, and the like.

The terminal control unit 36 controls each unit of the information terminal 3 on the basis of a control program stored in advance and information terminal control information input by the user through the input device 37.

Although not illustrated, a terminal-side storage unit is connected to the terminal control unit 36. The terminal-side storage unit stores a control program and the like of the information terminal 3. Here, as the terminal-side storage unit, for example, recording media such as a flash memory, a hard disk drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), and a universal serial bus memory (USB memory), a server, or the like can be used.

The terminal-side processor 38 having the communication control unit 32, the image decompression unit 33, the display control unit 34, and the terminal control unit 36 is configured by a CPU and a control program causing the CPU to execute various kinds of processing, but may be configured by using FPGA, DSP, ASIC, GPU, or other ICs, or may be configured by a combination thereof.

In addition, the communication control unit 32, the image decompression unit 33, the display control unit 34, and the terminal control unit 36 of the terminal-side processor 38 can also be configured by being integrated partially or entirely into one CPU or the like.

Figure 5:
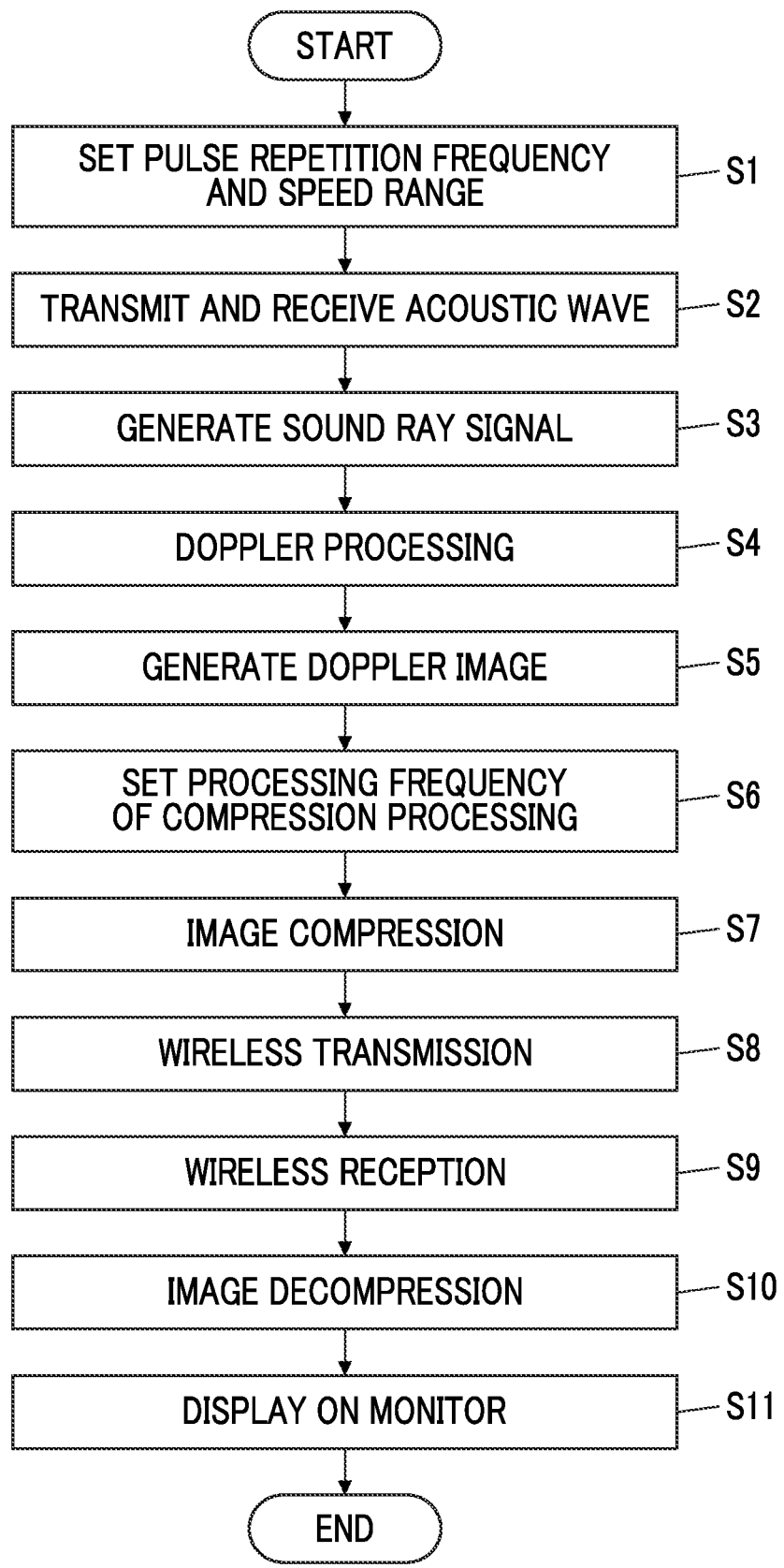
FIG. 5 is a flowchart illustrating an operation of the acoustic wave diagnostic apparatus in the first embodiment of the present invention.

Next, the operation of the acoustic wave diagnostic apparatus 1 in the first embodiment of the present invention will be described using the flowchart illustrated in FIG. 5. For the description, it is assumed that the pulsed wave Doppler mode is set as the inspection mode, and the Doppler image UD is generated as the acoustic wave image. Further, it is assumed that the Doppler image UD representing the speed of the moving object in the subject, which is generated by the Doppler image generation unit 16, is already displayed on the monitor 35 of the information terminal 3.

In Step S1, the pulse repetition frequency PRF of the ultrasonic pulse generated from the transducer array 11 and the speed range in the Doppler image UD are set by the user through the input device 37. Here, in general, it is known that, in a case where the Doppler shift frequency is greater than a half frequency of the pulse repetition frequency PRF, which corresponds to the so-called Nyquist frequency, in the Doppler image UD, a folding phenomenon occurs in which the Doppler waveform WD is folded back based on a speed value corresponding to the half frequency of the pulse repetition frequency PRF.

Therefore, it is desirable that the user sets the pulse repetition frequency PRF to about twice the maximum value of the Doppler shift frequency such that the folding phenomenon does not occur in the Doppler waveform WD in the Doppler image UD. Since the pulse repetition frequency PRF is equal to the processing frequency F1 of the Doppler processing in the Doppler processing unit 15 in the pulsed wave Doppler mode, the processing frequency F1 of the Doppler processing is also set to about twice the maximum value of the Doppler shift frequency, similarly to the pulse repetition frequency PRF.

Further, the user checks the Doppler image UD displayed on the monitor 35, and sets the speed range such that the Doppler waveform WD is within the Doppler image UD. In this case, it is desirable that the upper limit value and the lower limit value of the speed range are set to about the speed value corresponding to the maximum value of the Doppler shift frequency in the absolute value such that the Doppler waveform WD is displayed large in the Doppler image UD.

In this manner, in a case where the pulse repetition frequency PRF and the speed range in the Doppler image UD are set, the processing proceeds to Step S2, and the transmission and reception of the acoustic waves are performed in the acoustic wave probe 2. First, the acoustic wave probe 2 is brought into contact with the body surface of the subject by the user, the ultrasonic pulse is generated from the plurality of transducers of the transducer array 11 with the pulse repetition frequency PRF set in Step S1, according to the drive signal from the transmission circuit 12 under the control of the acoustic wave transmission and reception control unit 14, and the ultrasound beam is transmitted into the subject by the combined wave of the ultrasonic pulses. The ultrasound echo based on the transmitted ultrasound beam is received by each transducer, and a reception signal as an analog signal is generated.

In Step S3, the reception signal generated in Step S2 is amplified by being output to the amplification unit 41 of the reception circuit 13, and is subjected to the AD conversion in the AD conversion unit 42 so that the reception data is acquired. By performing the reception focusing processing on the reception data by the beam former 43, the sound ray signal is generated.

In subsequent Step S4, the Doppler processing unit 15 performs the Doppler processing on the sound ray signal generated in Step S3, according to the pulse repetition frequency PRF set in Step S1, that is, the processing frequency F1 to generate the Doppler data representing the speed of the moving object in the subject. In this case, in the Doppler processing unit 15, the detection unit 44 generates the complex baseband signal by performing quadrature detection processing on the sound ray signal generated in Step S3, the high-pass filter 45 removes the clutter signal from the generated complex baseband signal, and the FFT circuit 46 generates the spectrum signal for the Doppler shift frequency by performing the Fourier transform on the complex baseband signal output from the high-pass filter 45.

Further, the speed conversion circuit 47 can calculate the Doppler data as the information representing the speed of the moving object in the subject by the relationship of the speed V of the moving object=(C/2)×(fd/fs) by setting the Doppler shift frequency obtained by the FFT circuit 46 as fd, the frequency of the ultrasonic wave transmitted into the subject by the transducer array 11 as fs, the sound speed as C, and the speed of the moving object in the subject as V.

In Step S5, the Doppler image generation unit 16 generates the Doppler image UD by expressing the magnitude of each frequency component by brightness while aligning the Doppler data generated in Step S4 on the time axis.

Figure 6:
FIG. 6 is a diagram schematically illustrating an example of a Doppler image including noise.

Here, since the reception signal as the analog signal, the acoustic wave transmission and reception control reference clock, the sound ray signal as the digital signal, the Doppler data, and the like are weak signals, in a case where the reception circuit 13, the Doppler processing unit 15, the Doppler image generation unit 16, and the compression processing unit 17 are disposed on the same substrate 24, the reception signal, the acoustic wave transmission and reception control reference clock, the sound ray signal, the Doppler data, and the like are likely to be affected by noise caused by voltage fluctuations in each circuit disposed on the substrate 24 due to the operation of the compression processing of the compression processing unit 17. Therefore, as in the acoustic wave diagnostic apparatus 1 of the first embodiment, in the acoustic wave diagnostic apparatus in which the acoustic wave probe and the information terminal are connected to each other by wireless communication and the reception circuit, the Doppler processing unit, the Doppler image generation unit, and the compression processing unit are disposed on the same substrate, in some cases, a noise waveform WN caused by noise due to the compression processing is included in the Doppler image UD as illustrated in FIG. 6, for example. In the example illustrated in FIG. 6, the speed range in the Doppler image UD is −2 (m/s) to 2 (m/s), and the noise waveform WN is positioned in each of a range of −2 (m/s) to −1 (m/s) and a range of 1 (m/s) to 2 (m/s).

Specifically, for example, in a case where the Doppler image UD is compressed into a so-called JPEG format, since the compression processing is performed in block units of 8 pixels×8 pixels, the compression processing is performed until the Doppler data corresponding to one time of transmission of the ultrasonic pulse, that is, the Doppler data generated by one time of the Doppler processing in the Doppler processing unit is accumulated for 8 lines, and waiting is performed until the Doppler data is accumulated for 8 lines again, the compression processing and the waiting are repeatedly performed. Therefore, the processing frequency F2 of the compression processing is lower than the processing frequency F1 of the Doppler processing.

Since the circuit after the compression processing is operated once in a period in which the compression processing by the compression processing unit is performed (data is delivered to the wireless communication circuit during the operation of the compression processing), the voltage of each circuit on the substrate on which the compression processing unit is disposed fluctuates, and therefore, noise caused by the frequency of the compression processing by the compression processing unit is included in the reception signal, the acoustic wave transmission and reception control reference clock, the sound ray signal as the digital signal, Doppler data, and the like. The pulse repetition frequency PRF of the ultrasonic pulse, that is, the processing frequency F1 of the Doppler processing in the Doppler processing unit is preferably set to about twice the maximum value of the Doppler shift frequency in order to prevent the occurrence of the folding phenomenon in the Doppler waveform WD in the Doppler image UD, but in this case, for example, since the processing frequency F2 of the compression processing is lower than the processing frequency F1 of the Doppler processing, the noise waveform WN caused by the processing frequency F2 of the compression processing is drawn to overlap the Doppler waveform WD in the Doppler image UD, in some cases.

In Step S6, the processing frequency setting unit 19 sets the processing frequency F2 of the compression processing in the compression processing unit 17 such that the processing frequency F2 is a frequency higher than twice the processing frequency F1 of the Doppler processing set in Step S1. In the acoustic wave probe 2 according to the first embodiment of the present invention, the reception circuit 13, the Doppler processing unit 15, the Doppler image generation unit 16, and the compression processing unit 17 are disposed on the same substrate 24, but the frequency of noise caused by the processing frequency F2 of the compression processing can be set to a frequency much higher than the Doppler shift frequency by setting the processing frequency F2 of the compression processing in this manner, and the Doppler image UD can be generated without being bothered by noise caused by the compression processing. That is, in the Doppler image UD, the noise waveform WN caused by the processing frequency F2 of the compression processing is expelled to the higher speed side (high frequency side) than the Doppler waveform WD so that the noise waveform WN can be prevented from overlapping the Doppler waveform WD. Further, in a case where the upper limit value and the lower limit value of the speed range in the Doppler image UD are set to about the speed value corresponding to the maximum value of the Doppler shift frequency in the absolute value in Step S1, the noise waveform WN can be prevented from being drawn in the Doppler image UD.

As the method of realizing the processing frequency of the compression processing, for example, in the case of JPEG, the waiting time for 8 lines is distributed and waiting is performed in block units of 8×8, and there by the frequency can be increased.

In Step S7, the compression processing unit 17 compresses the Doppler image UD generated in Step S5 into a JPEG format or the like according to the processing frequency F2 set in Step S6 to reduce the information amount of the Doppler image UD.

In Step S8, the wireless communication circuit 18 of the acoustic wave probe 2 wirelessly transmits the Doppler image UD compressed in Step S7 to the wireless communication circuit 31 of the information terminal 3. In general, in the wireless communication, in a case where data with a large information amount is transmitted, it takes a lot of time to transmit the data, but the Doppler image UD is compressed in Step S7 so that the information amount thereof is reduced, and therefore, it is possible to suppress the occurrence of a time lag in the wireless transmission of the Doppler image UD.

In Step S9, the wireless communication circuit 31 of the information terminal 3 receives the compressed Doppler image UD that is wirelessly transmitted from the wireless communication circuit 18 of the acoustic wave probe 2.

In Step S10, the image decompression unit 33 decompresses the Doppler image UD received in Step S9 into a format before being compressed in Step S7.

In Step S11, the display control unit 34 performs predetermined processing on the Doppler image UD decompressed in Step S10, and displays the processed Doppler image UD on the monitor 35. Here, in the displayed Doppler image UD, the noise waveform WN caused by the compression processing of Step S7 does not overlap the Doppler waveform WD, and the influence of the noise of the compression processing on the Doppler image UD is suppressed.

As described above, with the acoustic wave probe 2 according to the first embodiment of the present invention, since the processing frequency F2 of the compression processing in the compression processing unit 17 is set to a frequency higher than twice the processing frequency F1 of the Doppler processing in the Doppler processing unit 15, even in a case where the reception circuit 13, the Doppler processing unit 15, the Doppler image generation unit 16, and the compression processing unit 17 are disposed on the same substrate 24, the influence of the noise caused by the processing frequency F2 of the compression processing, on the Doppler image UD generated by the Doppler image generation unit 16 can be suppressed.

The reception circuit 13, the Doppler processing unit 15, the Doppler image generation unit 16, and the compression processing unit 17 are disposed on the same substrate 24, but the acoustic wave transmission and reception control unit 14, the wireless communication circuit 18, the processing frequency setting unit 19, the wireless communication circuit 18, and the power supply circuit 22 can also be disposed on the substrate 24 in addition to the reception circuit 13, the Doppler processing unit 15, the Doppler image generation unit 16, and the compression processing unit 17. Even in this case, the influence of the noise caused by the processing frequency F2 of the compression processing, on the Doppler image UD generated by the Doppler image generation unit 16 can be suppressed.

It has been described that each of the pulse repetition frequency PRF of the ultrasonic pulse and the speed range in the Doppler image UD is set by the user's input operation through the input device 37, but the pulse repetition frequency PRF can be automatically set on the basis of the set speed range, for example. Since the pulse repetition frequency PRF is preferably set to about twice the Doppler shift frequency in order to prevent the folding phenomenon in the Doppler waveform WD in the Doppler image UD, or the upper limit value and the lower limit value of the speed range in the Doppler image UD are preferably set to about the speed value corresponding to the Doppler shift frequency in the absolute value in order to prevent the noise waveform WN caused by the processing frequency F2 of the compression processing in the compression processing unit 17 from being drawn in the Doppler image UD, for example, the pulse repetition frequency PRF can be set to about twice the frequency corresponding to the upper limit value and the lower limit value of the set speed range. In this manner, the time and effort of the user to set the pulse repetition frequency PRF is reduced, and the noise waveform WN caused by the processing frequency F2 of the compression processing can be easily prevented from being drawn in the Doppler image UD.

It has been described that the Doppler image UD is generated in the pulsed wave Doppler mode, but the Doppler image UD can be generated in a so-called continuous wave Doppler mode. In this case, for example, a sampling frequency set in advance in the Doppler processing unit 15 or a sampling frequency set by the user through the input device 37 can be the processing frequency F1 of the Doppler processing. The sampling frequency set in this manner is preferably set to about twice the maximum value of the Doppler shift frequency in order to prevent the occurrence of the folding phenomenon in the Doppler waveform WD in the Doppler image UD. In this manner, even in a case where the continuous wave Doppler mode is set as the inspection mode, since the processing frequency F2 of the compression processing is set to a frequency higher than twice the processing frequency F1 of the Doppler processing, the influence of the noise caused by the processing frequency F2 of the compression processing, on the Doppler image UD generated by the Doppler image generation unit 16 can be suppressed.

It has been described that the acoustic wave probe 2 emits the ultrasonic waves as the acoustic waves, but the type of acoustic waves is not limited to the ultrasonic waves. For example, acoustic wave may be a sound wave in an audible region.

Further, a so-called laser Doppler image can also be generated as the acoustic wave image by providing a laser light source to the acoustic wave probe 2, irradiating the subject with laser light, and using a photoacoustic wave caused by vibration of the tissue inside the subject irradiated with the laser light. In this manner, even in a case where the laser Doppler image is generated as the acoustic wave image, with the acoustic wave probe 2 of the present invention, the influence of the noise caused by the processing frequency F2 of the compression processing, on the laser Doppler image can be suppressed.

Second Embodiment

In the first embodiment, it has been described that in a case where the reception circuit 13, the Doppler processing unit 15, the Doppler image generation unit 16, and the compression processing unit 17 are disposed on the same substrate 24, the compression processing of the compression processing unit 17 on the Doppler image UD causes noise to be included in the Doppler image UD, but on the same substrate 24, the compression processing performed on the B-mode image or the like other than the Doppler image UD also causes noise to be included in the Doppler image UD.

Figure 7:
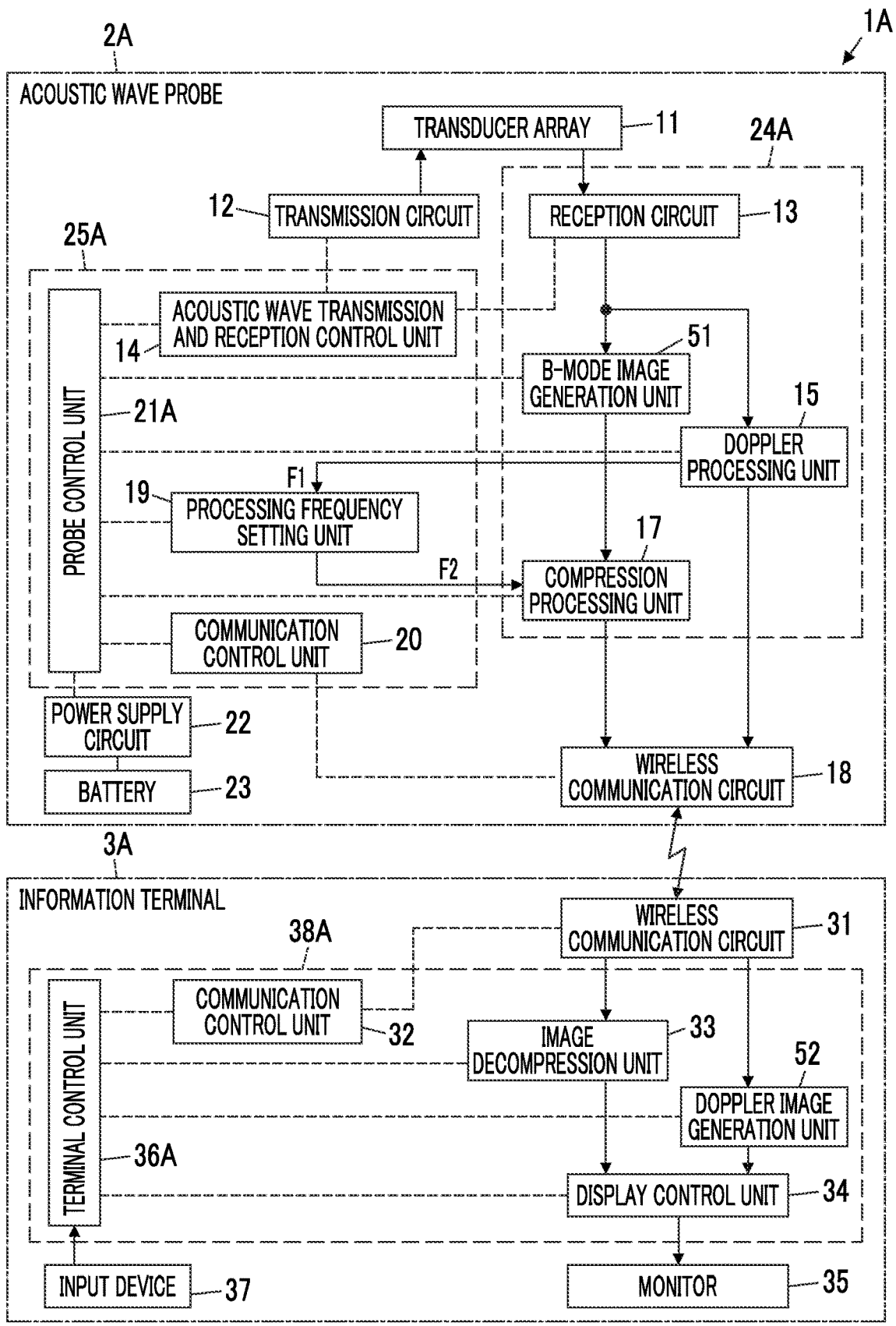
FIG. 7 is a block diagram illustrating a configuration of an acoustic wave diagnostic apparatus in a second embodiment of the present invention.

As illustrated in FIG. 7, an acoustic wave diagnostic apparatus 1A in a second embodiment of the present invention is obtained by comprising an acoustic wave probe 2A instead of the acoustic wave probe 2 and comprising an information terminal 3A instead of the information terminal 3 in the acoustic wave diagnostic apparatus 1 in the first embodiment illustrated in FIG. 1.

The acoustic wave probe 2A according to the second embodiment is obtained by excluding the Doppler image generation unit 16, adding a B-mode image generation unit 51, comprising a probe control unit 21A instead of the probe control unit 21, comprising a substrate 24A instead of the substrate 24, and comprising a probe-side processor 25A instead of the probe-side processor 25 in the acoustic wave probe 2 according to the first embodiment.

In the acoustic wave probe 2A, the Doppler processing unit 15 and the B-mode image generation unit 51 are connected to the reception circuit 13, and the compression processing unit 17 and the wireless communication circuit 18 are sequentially connected to the B-mode image generation unit 51. The probe control unit 21A is connected to the B-mode image generation unit 51. The wireless communication circuit 18 and the processing frequency setting unit 19 are connected to the Doppler processing unit 15. Further, the reception circuit 13, the Doppler processing unit 15, the compression processing unit 17, and the B-mode image generation unit 51 are disposed on the same substrate 24A.

The information terminal 3A in the second embodiment is obtained by adding a Doppler image generation unit 52, comprising a terminal control unit 36A instead of the terminal control unit 36, and comprising a terminal-side processor 38A instead of the terminal-side processor 38 in the information terminal 3 in the first embodiment. Here, the Doppler image generation unit 52 is the same as the Doppler image generation unit 16 of the acoustic wave probe 2 according to the first embodiment.

In the information terminal 3A, the image decompression unit 33 and the Doppler image generation unit 52 are connected to the wireless communication circuit 31, and the display control unit 34 is connected to the image decompression unit 33 and the Doppler image generation unit 52. The terminal control unit 36A is connected to the Doppler image generation unit 52.

Figure 8:
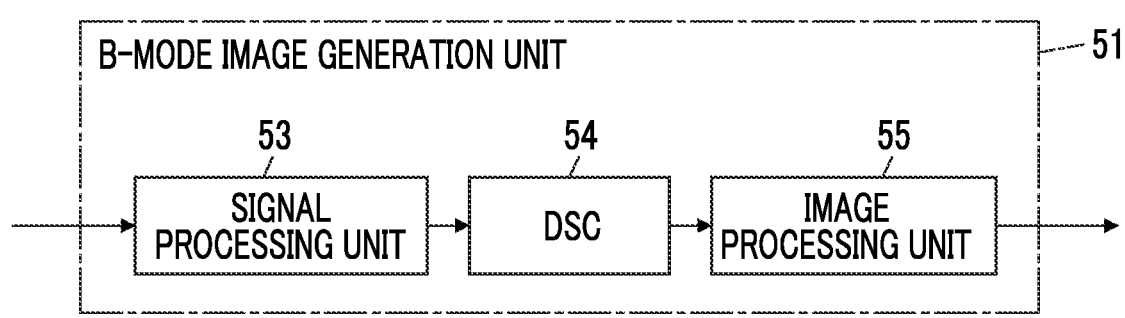
FIG. 8 is a block diagram illustrating an internal configuration of a B-mode image generation unit in the second embodiment of the present invention.

The B-mode image generation unit 51 of the acoustic wave probe 2A generates a B-mode image on the basis of the sound ray signal generated by the reception circuit 13, and has a configuration in which a signal processing unit 53, a digital scan converter (DSC) 54, and an image processing unit 55 are sequentially connected as illustrated in FIG. 8.

The signal processing unit 53 generates a B-mode image signal, which is tomographic image information regarding tissues inside the subject, by performing, on the sound ray signal generated by the reception circuit 13, correction of the attenuation due to the distance according to the depth of the reflection position of the ultrasonic wave and then performing envelope detection processing.

The DSC 54 converts (raster conversion) the B-mode image signal generated by the signal processing unit 53 into an image signal according to a normal television signal scanning method.

The image processing unit 55 performs various kinds of necessary image processing such as gradation processing on the B-mode image signal input from the DSC 54, and then sends the B-mode image signal to the compression processing unit 17. The B-mode image signal generated in such a manner is simply referred to as a B-mode image.

The Doppler processing unit 15 performs Doppler processing on the sound ray signal generated by the reception circuit 13 according to the processing frequency F1 to generate Doppler data. The Doppler data generated in this manner is sent to the wireless communication circuit 18.

The processing frequency setting unit 19 sets the processing frequency F2 of the compression processing in the compression processing unit 17 to a frequency higher than twice the processing frequency F1 of the Doppler processing in the Doppler processing unit 15.

The compression processing unit 17 compresses the B-mode image generated by the B-mode image generation unit 51 into a JPEG format or the like according to the processing frequency F2 set by the processing frequency setting unit 19. Here, since the voltage in each circuit on the substrate 24A fluctuates at the timing before and after the compression processing is performed on the B-mode image by the compression processing unit 17, noise caused by the compression processing is included in the reception signal as the analog signal, the acoustic wave transmission and reception control reference clock, the sound ray signal as the digital signal, the Doppler data, and the like. However, since the processing frequency F2 of the compression processing in the compression processing unit 17 is set to a frequency higher than twice the processing frequency F1 of the Doppler processing in the Doppler processing unit 15, the frequency of noise caused by the compression processing on the B-mode image becomes a frequency much higher than the Doppler shift frequency.

The wireless communication circuit 18 of the acoustic wave probe 2A wirelessly transmits the Doppler data generated by the Doppler processing unit 15 and the B-mode image compressed by the compression processing unit 17 to the wireless communication circuit 31 of the information terminal 3A under the control of the communication control unit 20.

The wireless communication circuit 31 of the information terminal 3A receives the Doppler data and the compressed B-mode image wirelessly transmitted by the wireless communication circuit 18 of the acoustic wave probe 2A, under the control of the communication control unit 32. Further, the wireless communication circuit 31 of the information terminal 3A sends the Doppler data to the Doppler image generation unit 52, and sends the compressed B-mode image to the image decompression unit 33.

The image decompression unit 33 decompresses the B-mode image sent from the wireless communication circuit 31 of the information terminal 3A into a format before being compressed by the compression processing unit 17.

The Doppler image generation unit 52 generates the Doppler image UD on the basis of the Doppler data sent from the wireless communication circuit 31 of the information terminal 3A. The Doppler data sent from the wireless communication circuit 31 of the information terminal 3A includes noise caused by the processing frequency F2 of the compression processing of the compression processing unit 17, but the frequency of the noise is a frequency much higher than the Doppler shift frequency, so that in the Doppler image UD generated by the Doppler image generation unit 52, the noise waveform WN caused by the noise is positioned on the higher speed side than the Doppler waveform WD and does not overlap the Doppler waveform WD. Further, in a case where the upper limit value and the lower limit value of the speed range in the Doppler image UD are set to about the maximum value of the Doppler shift frequency in the absolute value, the noise waveform WN can be prevented from being included in the Doppler image UD.

The display control unit 34 performs predetermined processing on the B-mode image decompressed by the image decompression unit 33 and the Doppler image UD generated by the Doppler image generation unit 52, and displays the B-mode image and the Doppler image UD on the monitor 35.

As described above, with the acoustic wave probe 2A according to the second embodiment of the present invention, similar to the acoustic wave probe 2 according to the first embodiment, since the processing frequency F2 of the compression processing in the compression processing unit 17 is set to a frequency higher than twice the processing frequency F1 of the Doppler processing in the Doppler processing unit 15 by the processing frequency setting unit 19, even in a case where the reception circuit 13, the Doppler processing unit 15, the compression processing unit 17, and the B-mode image generation unit 51 are disposed on the same substrate 24A and the B-mode image is compressed, the influence of the noise caused by the processing frequency F2 of the compression processing, on the Doppler image UD can be suppressed.

Third Embodiment

In the acoustic wave probe 2 according to the first embodiment, the compression processing is performed on the Doppler image UD, and in the acoustic wave probe 2A according to the second embodiment, the compression processing is performed on the B-mode image. However, the compression processing can be performed on both the Doppler image UD and the B-mode image.

Figure 9:
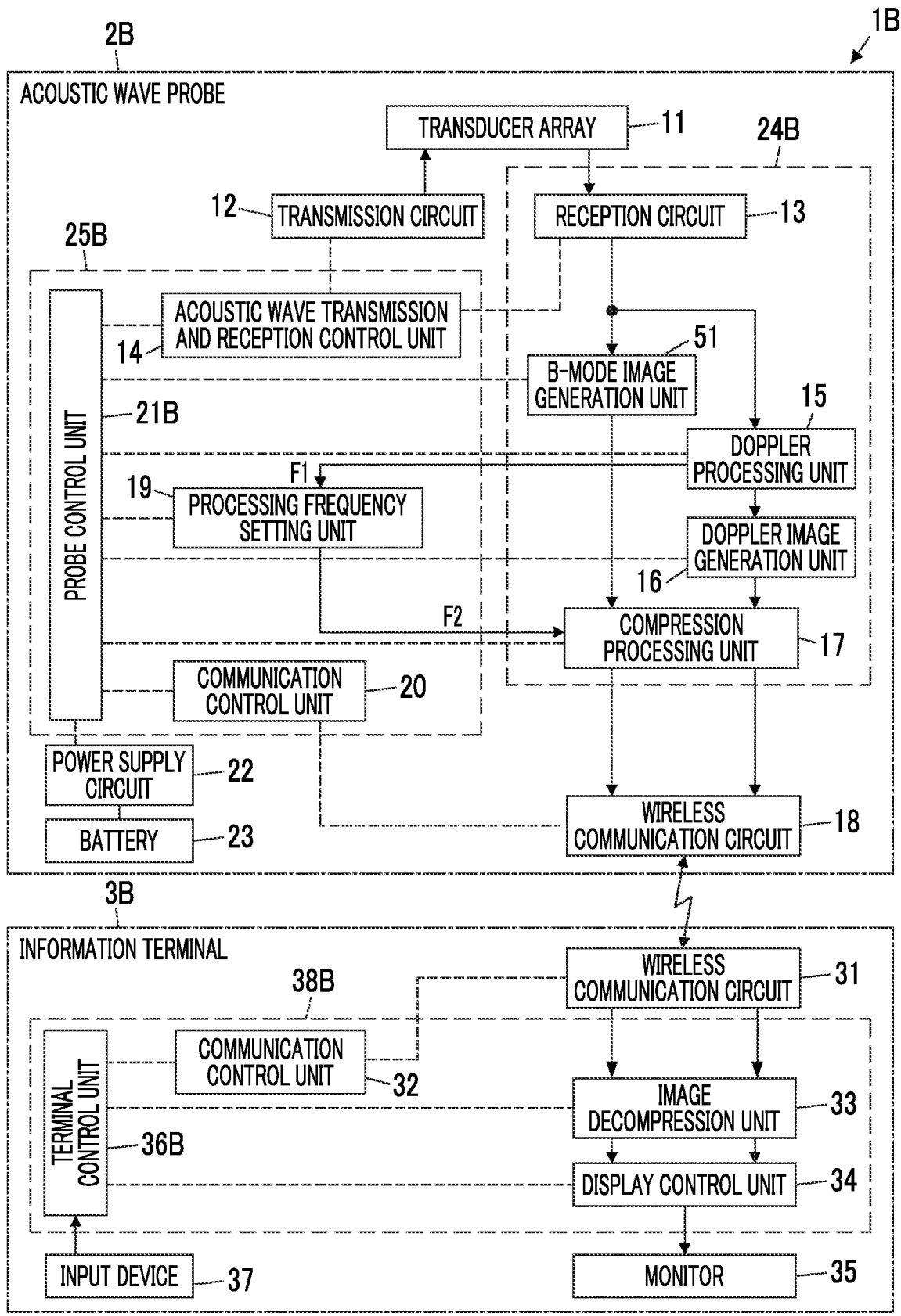
FIG. 9 is a block diagram illustrating a configuration of an acoustic wave diagnostic apparatus in a third embodiment of the present invention.

As illustrated in FIG. 9, an acoustic wave diagnostic apparatus 1B in a third embodiment is obtained by comprising an acoustic wave probe 2B instead of the acoustic wave probe 2 and comprising an information terminal 3B instead of the information terminal 3 in the acoustic wave diagnostic apparatus 1 in the first embodiment illustrated in FIG. 1.

The acoustic wave probe 2B according to the third embodiment is obtained by adding the B-mode image generation unit 51, comprising a probe control unit 21B instead of the probe control unit 21, comprising a substrate 24B instead of the substrate 24, and comprising a probe-side processor 25B instead of the probe-side processor 25 in the acoustic wave probe 2 according to the first embodiment.

In the acoustic wave probe 2B, the Doppler processing unit 15 and the B-mode image generation unit 51 are connected to the reception circuit 13, and the compression processing unit 17 and the probe control unit 21B are connected to the B-mode image generation unit 51. Further, the reception circuit 13, the Doppler processing unit 15, the Doppler image generation unit 16, the compression processing unit 17, and the B-mode image generation unit 51 are disposed on the same substrate 24B.

The information terminal 3B in the third embodiment is obtained by comprising a terminal control unit 36B instead of the terminal control unit 36, and comprising a terminal-side processor 38B instead of the terminal-side processor 38 in the information terminal 3 in the first embodiment.

The B-mode image generation unit 51 of the acoustic wave probe 2B generates the B-mode image on the basis of the sound ray signal generated by the reception circuit 13, and sends the generated B-mode image to the compression processing unit 17.

The Doppler processing unit 15 performs Doppler processing on the sound ray signal generated by the reception circuit 13 according to the processing frequency F1 to generate Doppler data.

The Doppler image generation unit 16 generates the Doppler image UD on the basis of the Doppler data generated by the Doppler processing unit 15.

The processing frequency setting unit 19 sets the processing frequency F2 of the compression processing in the compression processing unit 17 to a frequency higher than the processing frequency F1 of the Doppler processing in the Doppler processing unit 15.

The compression processing unit 17 compresses the B-mode image generated by the B-mode image generation unit 51 and the Doppler image UD generated by the Doppler image generation unit 16 into a JPEG format or the like according to the processing frequency F2 set by the processing frequency setting unit 19. Therefore, the frequency of the noise caused by the processing frequency F2 of the compression processing, which is included in the Doppler data generated by the Doppler processing unit 15 becomes a frequency much higher than the Doppler shift frequency, and thus, in the Doppler image UD generated by the Doppler image generation unit 16, the noise waveform WN caused by the noise is positioned on the higher speed side than the Doppler waveform WD without overlapping the Doppler waveform WD. Further, in a case where the upper limit value and the lower limit value of the speed range in the Doppler image UD are set to about the maximum value of the Doppler shift frequency in the absolute value, the noise waveform WN can be prevented from being included in the Doppler image UD.

The wireless communication circuit 18 of the acoustic wave probe 2B wirelessly transmits the Doppler image UD and the B-mode image that are compressed by the compression processing unit 17, to the wireless communication circuit 31 of the information terminal 3B.

The wireless communication circuit 31 of the information terminal 3B receives the compressed Doppler image UD and B-mode image, which are wirelessly transmitted by the wireless communication circuit 18 of the acoustic wave probe 2B, and sends the compressed Doppler image UD and B-mode image to the image decompression unit 33.

The image decompression unit 33 decompresses the Doppler image UD and the B-mode image sent from the wireless communication circuit 31 of the information terminal 3B into a format before being compressed by the compression processing unit 17, and sends the decompressed Doppler image UD and B-mode image to the display control unit 34.

The display control unit 34 performs predetermined processing on the Doppler image UD and the B-mode image sent from the image decompression unit 33, and displays the Doppler image UD and the B-mode image on the monitor 35.

As described above, with the acoustic wave probe 2B according to the third embodiment of the present invention, similar to the acoustic wave probe 2 according to the first embodiment, since the processing frequency F2 of the compression processing in the compression processing unit 17 is set to a frequency higher than twice the processing frequency F1 of the Doppler processing in the Doppler processing unit 15 by the processing frequency setting unit 19, even in a case where the reception circuit 13, the Doppler processing unit 15, the Doppler image generation unit 16, the compression processing unit 17, and the B-mode image generation unit 51 are disposed on the same substrate 24B, the influence of the noise caused by the processing frequency F2 of the compression processing, on the Doppler image UD can be suppressed.

Fourth Embodiment

In the acoustic wave diagnostic apparatus 1 in the first embodiment, the acoustic wave probe 2 and the information terminal 3 are connected to each other by wireless communication, but may be further connected by wired communication.

Figure 10:
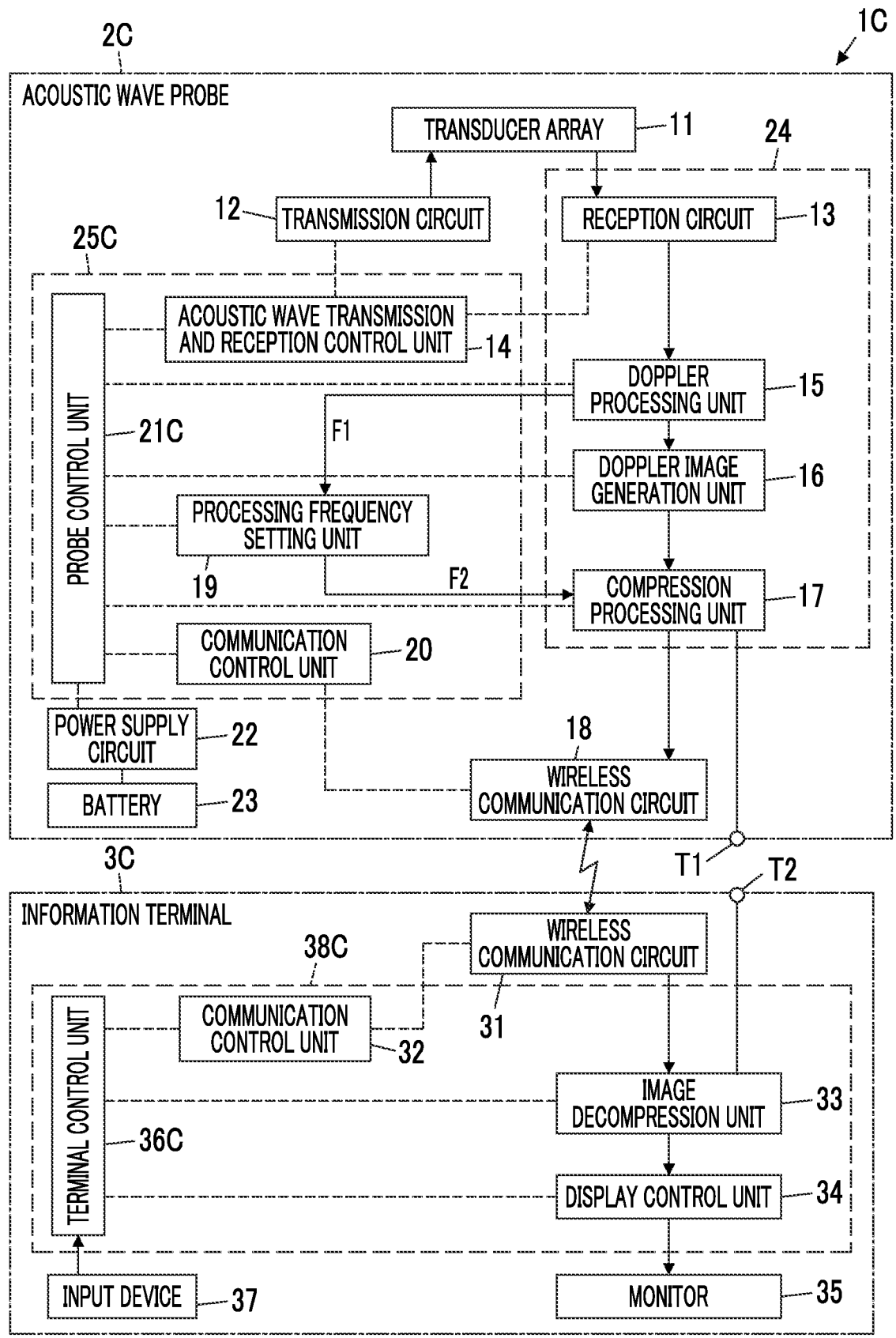
FIG. 10 is a block diagram illustrating a configuration of an acoustic wave diagnostic apparatus in a fourth embodiment of the present invention.

As illustrated in FIG. 10, an acoustic wave diagnostic apparatus 1C in a fourth embodiment is obtained by comprising an acoustic wave probe 2C instead of the acoustic wave probe 2 and comprising an information terminal 3C instead of the information terminal 3 in the acoustic wave diagnostic apparatus 1 in the first embodiment illustrated in FIG. 1.

The acoustic wave probe 2C according to the fourth embodiment is obtained by adding a wired connection terminal T1, comprising a probe control unit 21C instead of the probe control unit 21, and comprising a probe-side processor 25C instead of the probe-side processor 25 in the acoustic wave probe 2 according to the first embodiment. In the acoustic wave probe 2C, the wired connection terminal T1 is connected to the compression processing unit 17.

The information terminal 3C in the fourth embodiment is obtained by adding a wired connection terminal T2, comprising a terminal control unit 36C instead of the terminal control unit 36, and comprising a terminal-side processor 38C instead of the terminal-side processor 38 in the information terminal 3 in the first embodiment. In the information terminal 3C, the wired connection terminal T2 is connected to the image decompression unit 33.

The wired connection terminal T1 of the acoustic wave probe 2C and the wired connection terminal T2 of the information terminal 3C can be connected to each other in a wired manner by a cable or the like (not illustrated). In this manner, in a state where the wired connection terminal T1 of the acoustic wave probe 2C and the wired connection terminal T2 of the information terminal 3C are connected to each other in a wired manner, bidirectional data transmission is possible by a cable connected to the wired connection terminals T1 and T2. For example, the Doppler image UD compressed by the compression processing unit 17 of the acoustic wave probe 2C is transmitted to the image decompression unit 33 of the information terminal 3C via the cable connected to the wired connection terminals T1 and T2.

In this manner, even in a case where the acoustic wave probe 2C and the information terminal 3C are connected to each other in a wired manner, with the acoustic wave probe 2C according to the fourth embodiment of the present invention, similar to the acoustic wave probe 2 according to the first embodiment, since the processing frequency F2 of the compression processing in the compression processing unit 17 is set to a frequency higher than twice the processing frequency F1 of the Doppler processing in the Doppler processing unit 15 by the processing frequency setting unit 19, the influence of the noise caused by the processing frequency F2 of the compression processing, on the Doppler image UD can be suppressed.

Further, it has been described that the form of the fourth embodiment is applied to the first embodiment, but the form of the fourth embodiment can be similarly applied to the second embodiment and the third embodiment.

EXPLANATION OF REFERENCES 1, 1A, 1B, 1C: acoustic wave diagnostic apparatus
2, 2A, 2B, 2C: acoustic wave probe
3, 3A, 3B, 3C: information terminal
11: transducer array
12: transmission circuit
13: reception circuit
14: acoustic wave transmission and reception control unit
15: Doppler processing unit
16, 52: Doppler image generation unit
17: compression processing unit
18, 31: wireless communication circuit
20, 32: communication control unit
21: probe control unit
22: power supply circuit
23: battery
24, 24A, 24B, 24C: substrate
25, 25A, 25B, 25C: probe-side processor
33: image decompression unit
34: display control unit 35: monitor
36, 36A, 36B, 36C: terminal control unit
37: input device
38, 38A, 38B, 38C: terminal-side processor
41: amplification unit
42: AD conversion unit
43: beam former
44: detection unit
45: high-pass filter
46: FFT circuit
47: speed conversion circuit
51: B-mode image generation unit
53: signal processing unit
54: DSC
55: image processing unit
T1, T2: wired connection terminal
UD: Doppler image
WD: Doppler waveform
WN: noise waveform

What is claimed is:

1. An acoustic wave probe wirelessly connected to an information terminal, the acoustic wave probe comprising:
a transducer array;
a transmission circuit configured to cause the transducer array to transmit an acoustic wave;
a reception circuit configured to
perform digital conversion of an analog reception signal acquired by the transducer array that has received an acoustic wave echo, and
perform reception focusing processing to generate a sound ray signal;
a processor configured to
perform Doppler processing based on the sound ray signal generated by the reception circuit to generate Doppler data,
generate a Doppler image based on the Doppler data,
perform compression processing to compress the Doppler image, and
set a processing frequency F2 of the compression processing such that the processing frequency F2 becomes a frequency higher than twice a processing frequency F1 of the Doppler processing;
a wireless communication circuit configured to transmit the Doppler image which is compressed to the information terminal; and
wherein at least the reception circuit and the processor are disposed on the same substrate, and
the processing frequency F1 is equal to a pulse repetition frequency.

2. An acoustic wave probe wirelessly connected to an information terminal, the acoustic wave probe comprising:
a transducer array;
a transmission circuit configured to cause the transducer array to transmit an acoustic wave;
a reception circuit configured to
perform digital conversion of an analog reception signal acquired by the transducer array that has received an acoustic wave echo, and
perform reception focusing processing to generate a sound ray signal;
a processor configured to
generate Doppler data based on the sound ray signal generated by the reception circuit,
generate a B-mode image based on the sound ray signal, perform compression processing to compress the B-mode image, and
set a processing frequency F2 of the compression processing such that the processing frequency F2 becomes a frequency higher than twice a processing frequency F1 of the Doppler processing;
a wireless communication circuit configured to transmit the Doppler data and the B-mode image which is compressed to the information terminal; and
wherein at least the reception circuit and the processor are disposed on the same substrate, and
the processing frequency F1 is equal to a pulse repetition frequency.

3. The acoustic wave probe according to claim 2,
wherein the processor is further configured to
generate a Doppler image based on the Doppler data,
further compress the Doppler image, and
the wireless communication circuit is further configured to wirelessly transmit the Doppler image which are compressed.

4. The acoustic wave probe according to claim 3,
wherein the processor is disposed on the substrate.

5. The acoustic wave probe according to claim 1,
wherein the processor is further configured to control transmission of the acoustic wave by the transmission circuit and reception of the acoustic wave echo by the reception circuit.

6. The acoustic wave probe according to claim 2,
wherein the processor is further configured to control transmission of the acoustic wave by the transmission circuit and reception of the acoustic wave echo by the reception circuit.

7. The acoustic wave probe according to claim 3,
wherein the processor is further configured to control transmission of the acoustic wave by the transmission circuit and reception of the acoustic wave echo by the reception circuit.

8. The acoustic wave probe according to claim 4,
wherein the processor is further configured to control transmission of the acoustic wave by the transmission circuit and reception of the acoustic wave echo by the reception circuit.

9. The acoustic wave probe according to claim 5, further comprising:
a battery; and
a power supply circuit configured to supply power from the battery into the acoustic wave probe.

10. The acoustic wave probe according to claim 6, further comprising:
a battery; and
a power supply circuit configured to supply power from the battery into the acoustic wave probe.

11. The acoustic wave probe according to claim 9,
wherein the power supply circuit is disposed on the substrate.

12. The acoustic wave probe according to claim 10,
wherein the power supply circuit is disposed on the substrate.

13. The acoustic wave probe according to claim 1,
wherein the wireless communication circuit is disposed on the substrate.

14. The acoustic wave probe according to claim 2,
wherein the wireless communication circuit is disposed on the substrate.

15. The acoustic wave probe according to claim 3,
wherein the wireless communication circuit is disposed on the substrate.

16. The acoustic wave probe according to claim 4,
wherein the wireless communication circuit is disposed on the substrate.

17. The acoustic wave probe according to claim 1, further comprising:
a wired connection terminal for wired connection with the information terminal.

18. The acoustic wave probe according to claim 1,
wherein the processor is further configured to generate continuous wave Doppler data or pulsed Doppler data.

19. A control method of an acoustic wave probe which is wirelessly connected to an information terminal and in which at least a reception circuit and a processor are disposed on the same substrate, the control method comprising:
causing a transducer array of the acoustic wave probe to transmit an acoustic wave;
causing the reception circuit to
perform digital conversion of an analog reception signal acquired by the transducer array that has received an acoustic wave echo, and
perform reception focusing processing to generate a sound ray signal;
causing the processor to
perform Doppler processing based on the sound ray signal to generate Doppler data;
generate a Doppler image based on the Doppler data;
perform compression processing to compress the Doppler image;
set a processing frequency F2 of the compression processing such that the processing frequency F2 becomes a frequency higher than twice a processing frequency F1 of the Doppler processing; and
wirelessly transmitting the Doppler image which is compressed to the information terminal, and
the processing frequency F1 is equal to a pulse repetition frequency.

20. A control method of an acoustic wave probe which is wirelessly connected to an information terminal and in which at least a reception circuit and a processor are disposed on the same substrate, the control method comprising:
causing a transducer array of the acoustic wave probe to transmit an acoustic wave;
causing the reception circuit to
perform digital conversion of an analog reception signal acquired by the transducer array that has received an acoustic wave echo, and
perform reception focusing processing to generate a sound ray signal;
causing the processor to
perform Doppler processing based on the sound ray signal to generate Doppler data;
generate a B-mode image based on the sound ray signal;
perform compression processing to compress the B-mode image;
set a processing frequency F2 of the compression processing such that the processing frequency F2 becomes a frequency higher than twice a processing frequency F1 of the Doppler processing; and
wirelessly transmitting the Doppler data and the B-mode image which is compressed to the information terminal, and
the processing frequency F1 is equal to a pulse repetition frequency.

* * * * *